United States Patent
Koç et al.

(10) Patent No.: US 9,851,706 B2
(45) Date of Patent: Dec. 26, 2017

(54) ARTIFICIAL HOLLOW BIOLOGICAL TISSUE NETWORK AND METHOD FOR PREPARATION THEREOF

(71) Applicant: SABANCI ÜNIVERSITESI, Istanbul (TR)

(72) Inventors: Bahattin Koç, Istanbul (TR); Can Küçükgül, Istanbul (TR); Saime Burçe Özler, Istanbul (TR)

(73) Assignee: SABANCI ÜNIVERSITESI, Tuzla, Istanbul (TR)

( * ) Notice: Subject to any disclaimer, the term of this patent is extended or adjusted under 35 U.S.C. 154(b) by 85 days.

(21) Appl. No.: 14/725,094

(22) Filed: May 29, 2015

(65) Prior Publication Data

US 2015/0342720 A1 Dec. 3, 2015

(30) Foreign Application Priority Data

May 29, 2014 (EP) .................................... 14170465

(51) Int. Cl.
| | |
|---|---|
| *A61F 2/06* | (2013.01) |
| *G05B 17/00* | (2006.01) |
| *C12N 5/071* | (2010.01) |
| *G06F 19/00* | (2011.01) |
| *A61L 27/50* | (2006.01) |
| *C12M 3/00* | (2006.01) |
| *C12M 1/26* | (2006.01) |
| *A61L 27/38* | (2006.01) |

(52) U.S. Cl.
CPC .............. *G05B 17/00* (2013.01); *A61F 2/062* (2013.01); *A61L 27/3886* (2013.01); *A61L 27/507* (2013.01); *C12M 21/08* (2013.01); *C12M 33/00* (2013.01); *C12N 5/0691* (2013.01); *G06F 19/3437* (2013.01); *A61F 2002/065* (2013.01); *C12N 2513/00* (2013.01)

(58) Field of Classification Search
CPC ............ A61F 2/062; A61F 2/06; G05B 17/00
See application file for complete search history.

(56) References Cited

PUBLICATIONS

Norotte, Cyrille, Scaffold-free vascular tissue engineering using bioprinting, Jun. 2009, Elsevier, vol. 30, 5910-5917.*

* cited by examiner

*Primary Examiner* — Thomas J Sweet
*Assistant Examiner* — Tiffany Shipmon
(74) *Attorney, Agent, or Firm* — Epstein Drangel LLP; Robert L. Epstein

(57) ABSTRACT

A network (100) for replacement of a living tissue, said network is a scaffold-free artificial hollow biological tissue network comprising a plurality of longitudinal multicellular aggregates (11) arranged in a plurality of bioprinted layers (22) which are located on top of one another, further comprising an inner surface (20) and an outer surface (21), wherein at least one of said bioprinted layers (22) is in shape of a planar closed loop such that a conduit for conveying fluids is defined, and said longitudinal multicellular aggregate (11) is a mixture of at least two cell types. Also a method for obtaining said longitudinal multicellular aggregate, and a further method for biomodeling and planning said network are proposed.

8 Claims, 6 Drawing Sheets

ARTIFICIAL HOLLOW BIOLOGICAL TISSUE NETWORK AND METHOD FOR PREPARATION THEREOF

TECHNICAL FIELD OF THE INVENTION

The present invention relates to artificial biological tissue networks and a method for preparation thereof.

BACKGROUND OF THE INVENTION

Cardiovascular disease is the leading cause of deaths worldwide. The most common treatments for cardiovascular health diseases are autograft and blood vessel transplantation which has limitations due to lack of donors and the patients' conditions may not allow harvesting one. Additionally, extracting of an autograft may not be possible if all the possible grafts are extracted from the harvested site or the disease has already been advanced. One of the aims of tissue engineering is to provide a possible alternative for such grafts. Recently, tissue engineering and regenerative medicine aim to provide alternative treatments and fast recovery for the patients suffering from cardiovascular diseases. (doi: 10.1155/2012/956345)

Traditionally, tissue engineering strategies are based on the cell seeding into synthetic, biological or composite scaffolds providing a suitable environment for cell attachment, proliferation and differentiation. Cells are seeded into synthetic, biological or composite scaffolds which supply a suitable environment for cell attachment, proliferation and differentiation and have the same functional role as an extracellular matrix (ECM) until the cells create their own ECM. It is really challenging to seed the cells uniformly and selectively so they can attach and proliferate into the fabricated 3D scaffolds. In addition, the seeded scaffolds' degradation could cause immunogenic and unforeseen side effects after in-vivo implantation. In recent years, the scaffolds have been fabricated with controlled internal architecture using 3D printing techniques (doi: 10.1088/1758-5082/3/3/034106, doi: 10.1016/j.cad.2013.07.003).

Although 3D scaffolds are designed to act as an artificial ECM until the cells form their own ECM, it is challenging to fabricate a controlled porous structure with a desired internal architecture repetitively. In addition, functional vascularization of 3D scaffolds is compulsory needed for nutrition and oxygen supply to the engineered tissue. In order to provide nutrition and oxygen to the cells, different approaches based on endothelial cells or scaffolds are developed (doi: 10.1016/j.addr.2011.03.004).

To enable direct anastomosis of the scaffold to the host vasculature in vivo, self-assembly approach is used. In this approach, a bioprinted macrovascular network is matured in a perfusion reactor to achieve required mechanical properties. Microvascular units in the form of cylindrical or spherical multicellular aggregates are produced by the parenchymal and endothelial cells, placed in the macrovascular network and perfused to promote self-assembly and the connection to the existing network (doi: 10.1088/1758-5082/2/2/022001).

Despite several studies related with the vascular tissue engineering, it is still not achieved to construct an entirely biomimetic blood vessel due to the poor mechanical properties of the materials. Therefore, first applications of scaffold-based vascular grafts are tried under low pressure. The degradation of the materials and the cell-material interaction could cause unforeseen side effects including chronic inflammation, thrombosis and rejection after in-vivo implantation. Especially, weakness of cell to cell interaction and the assembly and alignment of ECM are critical in vascular tissue-engineering. Considering all these reasons, vascular tissue engineering studies tend towards scaffold-free techniques (U.S. Pat. No. 8,143,055 B2, US 2012 288 938 A1). In the artificial tissues according to the U.S. Pat. No. 8,143,055 B2, shape and orientation of branches are limited to be parallel with the flat surface on which the cell paste pieces of living cells and their support material pieces are laid. This is a highly binding limitation, which does not fit the natural organization of cells and the shapes of real blood vessels, which have generally uneven shapes and branch orientations.

Additionally, the longitudinal multicellular aggregate preparation method explained in said document requires several repetitive manual bioink preparation steps of multicellular aggregates into/from capillaries; which have to be performed with extreme precision; hence, the reproducibility and speed of said steps can be considered as low. Therefore an alternative method replacing said steps, thus minimizing the human intervention and maximizing the reproducibility is extremely important for bioprinting of said networks.

There has been few research working on building small-diameter, multi-layered, tubular vascular and nerve grafts. Multicellular spherical and cylindrical aggregates have been fabricated with 3D printing methods. Flexibility in tube diameter and wall thickness is obtained and most significantly branched macrovascular structures are constructed with this method (doi:10.1088/1758-5082/4/2/022001). In another study, human embryonic stem cell spheroid aggregates are formed with a valve-based cell printer and they have controllable and repeatable sizes. This work shows that the printed cells are mostly viable and have the potential to differentiate into any of the three germ layers (pluripotency) (doi:10.1088/1758-5082/5/1/015013). However, the preparation of large amounts of spherical aggregates is time-consuming and the fusion process of the spheroids takes 5-7 days. In addition, these approaches mostly require laborious bioink preparation and hence the presented methods can be considered rather unrepeatable and mostly rely on one's own skills.

Valve scaffold tissue engineering has the potential for fabricating blood vessels e.g. aortic valve hydrogel scaffolds that can grow, remodel and integrate with the patient. In order to mimic complex 3D anatomy and heterogeneity of e.g. an aortic valve, root wall and tri-leaflets are 3D printed with poly-ethylene-glycol-diacrylate (PEG-DA) hydrogels. Porcine aortic valve interstitial cells (PAVIC) seeded scaffolds maintained near 100% viability over 21 days (doi: 10.1088/1758-5082/4/3/035005). Another study demonstrates that encapsulated aortic root sinus smooth muscle cells (SMC) and aortic valve leaflet interstitial cells (VIC) are viable within the bioprinted alginate/gelatin aortic valve hydrogel conduits (doi: 10.1002/jbm.a.34420). Recently, human mesenchymal stem cells were encapsulated into agarose hydrogels and cell-laden hydrogel was 3D printed submerged in a hydrophobic high-density fluorocarbon, which mechanically supports the construct and afterwards can be easily removed. This method allows high stability to the printed structures, high cell viability, cell proliferation and production of ECM (doi: 10.1088/1758-5082/5/1/015003). However, the degradation of hydrogel material and formation of tissue structure can take a long time and some of the hydrogel material used could cause immune-reactions or side effects after degradation.

Prior art methods of preparation of multicellular aggregates for bioprinting have limited reproducibility, since said methods require substantial human intervention.

Although there are few studies relevant to the vascular tissue engineering, the poor mechanical strength of the materials contrasted with native vessels has limited the construction of an entirely biomimetic blood vessel. On that account, first implementations of scaffold-based vascular grafts are examined under low pressure (doi: 10.1016/j.biomaterials.2009.06.034).

OBJECTS OF THE INVENTION

Primary object of the present invention is to eliminate the above-mentioned shortcomings in the prior art.

Another object of the present invention is to provide a self-supporting scaffold-free artificial hollow biological tissue network for replacement of living tissue.

Further an object of the present invention is to provide an artificial biological tissue network with a high reproducibility and without requiring any manual intervention.

Still further an object of the present invention is to provide an artificial biological tissue network which is constructed in bottom-up direction.

Yet another object of the present invention is to provide an artificial biological tissue network which achieves a natural mechanical strength in a shorter time with respect to the prior art.

Another object of the present invention is to provide a method for obtaining such artificial biological tissue network directly based on medical images of the targeted tissue or organ.

A further object of the present invention is to provide a branched self-supporting scaffold-free artificial hollow biological tissue network for replacement of living tissue.

SUMMARY OF THE INVENTION

A network for replacement of a living tissue, said network is a scaffold-free artificial hollow biological tissue network comprising a plurality of longitudinal multicellular aggregates arranged in a plurality of bioprinted layers which are located on top of one another, further comprising an inner surface and an outer surface, at least one of said bioprinted layers is in shape of a planar closed loop such that a conduit for conveying fluids is defined, and said longitudinal multicellular aggregate is a mixture of at least two cell types. Also a method for obtaining said longitudinal multicellular aggregate, and a further method for biomodeling and planning said network are proposed.

BRIEF DESCRIPTION OF THE FIGURES

The figures whose brief explanations are herewith provided are solely intended for providing a better understanding of the present invention and are as such not intended to define the scope of protection or the context in which said scope is to be interpreted in the absence of the description.

DETAILED DESCRIPTION OF THE INVENTION

Referring now to the figures outlined above, the present invention proposes a self-supporting scaffold-free artificial hollow biological tissue network (also named as 'network' hereafter) explained in claim 1, which overcomes the above-mentioned shortcomings of the prior art. Said network (100) is shaped as a self-supporting three-dimensional (3D) bioprinted structure which is built from continuous longitudinal (e.g. cylindrical) multicellular aggregates of living cells, without employing any non-biological material e.g. scaffold remaining in contact with said network after implantation to a patient.

The term 'self-supporting' here means that the network (100) is supported by a removable plurality of support structures (12) as explained in this text, until the completion of the maturation process of said network, and after removal of support structures (12) the network (100) mainly comprises living cells fused and adhered in accordance with their natural abilities, which do not further require to be supported by any unnatural means e.g. scaffold.

The term 'multicellular' means that said aggregate comprises a plurality of living cells. Additionally, said aggregate is 'heterocellular' since it comprises a mixture comprising at least two cell types selected from a group comprising following cell types: fibroblasts, endothelial cells, smooth muscle and stem cells. A plurality of said longitudinal multicellular aggregates (11) are arranged in a plurality of bioprinted layers (22) which are located on top of one another, and at least one of said longitudinal multicellular aggregate layers is in shape of a planar closed loop such that a conduit for conveying fluids is defined.

Figure 6:
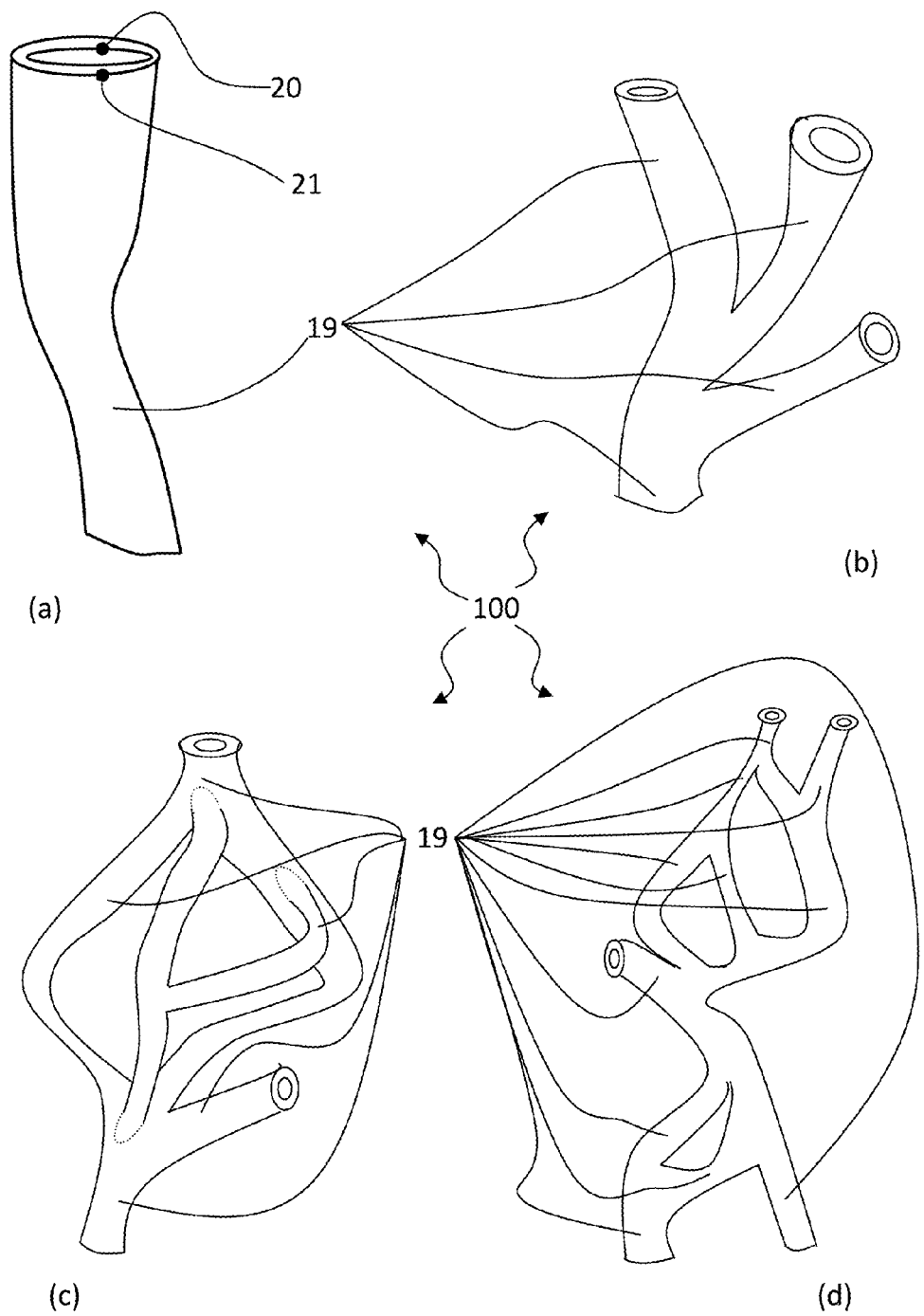
FIG. 6 (a-d) are schematic perspective drawings of self-supporting artificial hollow biological tissue networks according to the present invention, wherein (a) consists of a single branch and (b-d) are several examples of branched conduits with various levels of complexity.

In a preferred embodiment according to the present invention, said network (100) is a branched conduit, e.g. a branched blood vessel as shown in FIG. 6 (b-d). Such branched conduit comprises at least two branches (19) converged on at least one sector of said network.

Each closed loop of said longitudinal multicellular aggregate (11) can preferably be in contact with a support structure (12), which is biocompatible, bio-inert and also in form of longitudinal pieces, said contact is at both an inner surface (20) and an outer surface (21) of the network (100) for serving as a mold during a maturation process of the network. Said support structure (12) (e.g. hydrogel) serves for providing support during a maturation process of said network (100). Said support structure (12) can preferably comprise additional synthetic or biological substances for providing support to the viability of cells during the maturation of said network. Suitable substances to this end are known and available for a skilled person in the art.

Longitudinal geometry of said longitudinal multicellular aggregate (11) accelerates the maturation process of said network (100) since it facilitates perfusion between said cells in comparison with that between the cells in known spherical aggregates, thus the self-assembly, connection and partially cohesion of said cells is improved thanks to increased contact between adjacent bioprinted layers (22). In following exemplary experimental work in accordance with the present invention, cylindrical longitudinal multicellular aggregate with a closed-loop cross-section was chosen as said longitudinal geometry. Said closed-loop cross-section can have disk geometry as clearly shown in FIG. 5 (a), yet the longitudinal multicellular aggregate (11) can also have elliptical or other suitable closed-loop cross-section geometries besides of disk.

Each longitudinal multicellular aggregate (11) can preferably be in direct contact with at least one adjacent longitudinal multicellular aggregate (11) providing a cell-to-cell contact between said layers.

The longitudinal multicellular aggregates (11) in a bioprinted network (100) according to the present invention can be completely or partially cohered with each other.

Said longitudinal multicellular aggregate (11) has a length/diameter aspect ratio in the range of 20 to 250. Additionally, said longitudinal multicellular aggregate has a diameter within the range of 100 to 2500 micrometers.

In the exemplary experiment according to the present invention reported below, a 3D printer was used for depositing longitudinal multicellular aggregate (11) and the support structure (12) with its multiple deposition heads having capillaries. The capillaries for bearing and placing longitudinal multicellular aggregate (11) and support structure (12) can be made of glass or any other suitable bio-inert material e.g. steel or bio-inert polymers; and have inner diameters within the range of 100 to 2500 micrometers. In the exemplary experimental case reported below, the diameters of both capillaries for longitudinal multicellular aggregate (11) and support structure (12) were of about 500 µm.

While it is possible to control such printers with its own software for simple geometries, a novel path planning strategy for both longitudinal multicellular aggregate (11) and support structures (12) is developed for complex geometries. A 3D bioprinter can then be controlled directly by scripts generated by the methodology according to the present invention, and it can print longitudinal multicellular aggregates (11) and support structures (12) layer by layer to form desired tissue structures i.e. networks (100).

A biocompatible, bio-inert, thermo-reversible hydrogel e.g. agarose-based hydrogels can be used as support structure (12) for 3D printing of said network.

Exemplary experiment for obtainment of multicellular aggregates (11):

As the support structure (12), NovoGel (a commercial product by Organovo) was used for the experimental work explained below. NovoGel 2% (w/v) with phosphate buffered saline (PBS: Hyclone 1× by Thermo Scientific) with $Ca^{2+}$ and $Mg^{2+}$ salts solution was prepared by autoclaving it in accordance with standard liquid sterilization procedures. In order to print on a uniformly flat surface, 2% agarose solution with PBS was prepared first. After a sterilization process, 20 mL agarose solution is transferred into a petri dish bottom covering the entire dish bottom surface. A homemade Teflon mold which fits into the petri dish was sterilized and used for providing a flat surface. The mold was carefully put down onto the agarose inside the petri dish. Said mold was then carefully taken away from the petri dish after the agarose solution became completely solid gel. Prior to use of agarose mold for bioprinting, it was washed using PBS. During the materials preparation, adequate sterilization steps are followed to avoid any contamination.

In order to minimize/avoid human intervention, low reproducibility and long incubation periods caused by the repetitive aspiration/ejection steps of the methods of prior art which also slows down the bioprinting process, an automatized method for preparing longitudinal multicellular aggregates (11) and a bottom-up continuous bioprinting process preferably to be performed using an automated bioprinter having capillary(ies), was developed.

According to the present invention, a novel method for obtaining and forming longitudinal multicellular aggregate (11) from detached cells with reduced human intervention and increased reproducibility for use in production of a self-supporting scaffold-free artificial hollow biological tissue network (100) for replacement of living tissue, wherein said method comprises the following steps:

a) obtainment of a pellet of multicellular aggregate by subsequent centrifugation of detached cells, followed by removal of supernatant,
b) formation of said longitudinal multicellular aggregate (11) by aspirating a part of said pellet into a capillary.

The following sequential steps are preferably applied at least once between said steps 'a' and 'b' in order to allow said cells to aggregate and initiate cell-cell adhesions,
i) resuspension of said pellet and shaking of obtained suspension using a shaker in an incubator,
ii) re-obtainment of a pellet, by a sequence consisting of centrifugal of said resuspended cells and removal of supernatant.

For obtainment of longitudinal multicellular aggregates (11) comprising fibroblast, endothelial and smooth muscle cells, sequential application of above steps a, i, ii, b is required.

Even though said aspiration into capillary can be performed manually, an automated bioprinter having said capillary can preferably be employed. Employing an automated bioprinter in connection with said capillary even further reduces the human intervention at forming said longitudinal heterocellular aggregate (11) and even further increases the reproducibility. Said automated bioprinter working according to the method of the present invention, arranges in-capillary-formation of longitudinal multicellular aggregates (11) and support structures (12) having respective calculated lengths for each bioprinted layer (22), such that non-interrupted closed loops of longitudinal multicellular aggregates (11) and support structures (12) are formed.

Thus, in a preferred embodiment according to the present invention, said aspiration is performed using an automated bioprinter comprising said capillary, and said part fills a predetermined length of said capillary, which length is equal to a predetermined length of a longitudinal multicellular aggregate (11).

Such longitudinal multicellular aggregate (11) is suitable for use in obtainment of self supporting scaffold-free artificial biological tissue networks (100) according to the present invention. Said method is employed in an example experiment according to the present invention as follows:

In this exemplary experiment, a mixture comprising smooth muscle cells, endothelial cells and early passage human dermal fibroblast (HDF) cells were used. The percentage of each cell type in said heterocellular mixture is preferably decided based on the tissue type. In this exemplary experiment, 25% endothelial cells are mixed with 75% HDF cells to form heterocellular mixture. The cells were cultured at 37° C. and under 5% $CO_2$ using Dulbecco's Modified Eagle's Medium (DMEM, provided by Sigma, Germany) supplemented with 10% fetal bovine serum (FBS, provided by Sigma, Germany), 1% Penicillin-Streptomycin (provided by Sigma, Germany).

Each said cell types were cultured in tissue culture flasks. Following the removal of the culture medium from culture flasks, cells were washed with PBS. Said cells can be detached from the tissue culture flasks using two alternative ways: they can be either detached by incubating with trypsin solution from porcine pancreas (provided by Sigma, Germany) (the trypsin concentration was 1× and the contact time was 10 minutes), or by using cell scrapers. Following the detachment step, remaining trypsin was rinsed/neutralized using serum containing medium, and the cells were centrifuged at 200×g for 5 minutes, then supernatant was discarded thus a cell pellet is obtained. Said cell pellet was resuspended in 1 mL of culture medium and then transferred into T25 tissue culture flasks (TPP, Germany) containing 6 mL culture medium. T25 tissue culture flasks were incubated at 37° C. and 5% $CO_2$ on an orbital shaker and shaken at 160 rpm for 60 minutes. Following the above-explained shaking period, the cells were collected into 15 mL sterile falcon tubes and the collected cell suspensions were centrifuged at 200×g for 5 minutes. After removing the supernatant, the cell pellet was resuspended (for this experiment, in a 1 mL medium) and transferred into Eppendorf tubes (for this experiment, 1.5 ml) and centrifuged again at 1000×g for 4 minutes to form a dense cell pellet. After discarding the supernatant, cell pellets in the Eppendorf tubes were nonformed multicellular aggregates (pellets) to be aspired into capillaries for formation of longitudinal multicellular aggregates (11) for continuous bioprinting automatically according to the said developed algorithms. In a preferred embodiment according to the present invention, said aspiration and bioprinting are performed automatically by an automated bioprinter having a capillary(ies).

The bioprinted constructs were incubated for 1-7 days so that the longitudinal multicellular aggregates (11) fuse together, and an artificial biological tissue network (100) is formed. The formed biological tissue network is preferably put in a bioreactor where a flow of medium pass through to further mature the fused network (100) until the replacement of a targeted tissue is constituted.

Since real blood vessels have generally uneven shapes and branch orientations, the bottom-up bioprinting process/technique eliminates geometrical limitations, resulting in reproduction of unevenly shaped biological conduits with any orientation of branch(es) thereof. FIG. 6 (a-d) shows several schematic examples for artificial biological tissue networks (100) according to the present invention, which are of various levels of shape complexities.

Longitudinal multicellular aggregates (11) obtained with the method according to the present invention, are free of any coating. Thus, when bioprinting of a network (100) comprising superimposed longitudinal multicellular aggregates (11) is done, each bioprinted layer (22) of longitudinal multicellular aggregates (11) will be in a direct contact with adjacent bioprinted layers (22) free of any mass transfer barrier. This facilitates said bioprinted layers (22) to fuse together and contract, so that the constitution of a network (100) with a natural strength occurs in a shortened time in comparison with prior art methods, since the cells in adjacent bioprinted layers (22) are in contact with each other throughout the bioprinted network (100). Furthermore, the continuous longitudinal geometry of the longitudinal multicellular aggregate (11) provides a high number of neighboring cells in each layer, which further facilitates the constitution of the natural strength of said network (100) in a short time in comparison with the prior art.

A method for biomodeling and bioprinting a self-supporting scaffold-free artificial hollow biological tissue network (100) is also proposed. Said network (100) is for replacement of living tissue, and comprises continuous longitudinal multicellular aggregates (11) arranged in a plurality of bioprinted layers (22) which are located on top of one another, and wherein at least one of said bioprinted layers (22) is in shape of a closed loop such that a conduit for conveying gases and liquids is defined. Briefly, said method includes following steps:

a) Biomimetical modeling steps for obtaining a computer model of a targeted tissue, listed as follows:

Obtaining a series of medical images of a targeted tissue to be bioprinted,

Masking and segmenting a region from said images using suitable imaging software, Converting said segmented region into a three-dimensional (3D) mesh model (2) having polygon facets (8) all of which are also parts of adjacent facets (8) of a vertex (9), Defining edge section curves consisting of a bottom section curve (6) and (a) top section curve(s) (7) for use as starting and ending section curves (1) of the model, respectively, wherein a section curve (1) is a sequential array of once handled vertices (9) until a vertex (9) is passed through because of it is already handled (i.e. any calculation is made for said vertex (9)), and wherein a section is an iterative level where a respective section curve (1) is calculated, Selecting one of said bottom section curve (6) as a starting section curve for using as input, Marking each vertex (9) of said model (2) when each vertex (9) is subjected to calculations to form a section curve (1) with respect to a marching direction of said calculations, so that each vertex (9) is subjected to said calculations only once, Marking each section curve (1) and number of vertices (9) on each section curve (1), such that the calculations proceed to an adjacent uncalculated section curve (1) after subjecting each vertex (9) on a current section curve (1) to calculations once, thus obtaining a closed polyline curve as a section curve (1), If there are multiple section curves (1) resulted in calculation of a certain section, defining respective previously calculated section curve (1) as a starting point of a branch section curve, and defining branches (19) having the same count of said multiple section curves (1), Defining a respective center point (3) for each section curve (1) reflecting area weight-based center points for each corresponding section curve (1), Defining a respective radius value for each section curve (1) reflecting a radius of a maximally-inscribed sphere of each section curve (1), Calculating coordinates of a center point (3) for each section curve (1) for approximation of a centerline curve (10) for each branch (19) until their respective top section curves (7) are reached, Defining a top-most section curve (18) obtained following a highest number of previously calculated subsequent section curves (1) by comparing the count of section curves (1) in each branch (19); defining the top section curve (7) as top-most section curve (18) if there is only one section curve (1) in each calculative layer, Generating parametric surfaces (5) with calculated radii of section curves (1) along a trajectory of respective centerline curve(s) (10) for 3D bioprinting;

b) Path planning steps for layer-by-layer locating said longitudinal multicellular aggregates (11) and support structures (12) in form of longitudinal pieces made of bio-inert material for supporting said longitudinal multicellular aggregates (11) on a horizontal biocompatible substrate surface through respective support structures (12), from both an inner surface (20) and an outer surface (21) of the network (100), which support structures (12) mold said network (100) during a maturation process:

Calculating a total number of bioprinted layers (22) by dividing the distance between said top-most section curve (18) and said bottom curve (6) on said parametric surface (5) to the diameter of a respective longitudinal multicellular aggregate (11), Intersecting said parametric surface (5) with successive calculative layers (14) and obtaining respective contour curves for each calculative layer (14), Offsetting each contour curve with magnitude of diameter of longitudinal multicellular aggregate (11) until reaching a targeted network (100) thickness at respective bioprinted layers (22), such that the innermost diameter of each bioprinted layer (22) is not smaller than a corresponding inner diameter of targeted network (100) at respective bioprinted layers (22), Determining a number of closed-loop support structure layers which are to support said top curve (7) circumferentially from both inside (20) and outside (21) of said top curve (7). Said numbers can be different for said inside (20) and outside (21), For each bioprinted layer (22), calculating a number for outer support structure layers (23) covering/supporting the previously calculated curves of an adjacent upper layer circumferentially from outside (21), such that said number is obtained by iterative addition with at least '1' for each layer starting from said top layer (7) until said bottom layer (6), and with a starting value equal to the above determined number of outer support structure layers (23) supporting said network (100) from outside (21), For each layer, calculating a number of inner support structure layers (24) covering/supporting previously calculated curves of said adjacent upper layer circumferentially from inside (20), such that said number is obtained by iterative addition with '1' for each layer starting from said top layer (7) until said bottom layer (6), and such that iterative addition with '0' instead of '1' is applied if a number equal to the greatest integer value of division of a corresponding inner radius for a section curve (1) with radius of support structure (12) is reached for a layer, If multiple support structures (12) intersect in adjacency of a same bioprinted layer (22), forming a joint closed loop support structure at said layer by joining said multiple support structures (12), Determining lengths for longitudinal multicellular aggregates (11) and support structures (12) to be aspirated into capillaries and to be placed for constructing each respective bioprinted layer (22), Determining deposition coordinates for support structures (12) and longitudinal multicellular aggregates (11) in accordance with above steps, Generating and saving sequential commands for controlling a bioprinter to layer-by-layer deposition of support structures (12) and then of longitudinal multicellular aggregates (11) starting from said bottom layer (6), until said top-most layer (18), Sending said commands to a bioprinter.

The application of said method in our experiments is explained below in detail:

A medical image, which is preferably obtained using computer tomography (CT) or magnetic resonance imaging (MRI) is used to obtain geometric and topological information of targeted tissue (in this work, sample blood vessels, branched or unbranched). Secondly, the STL (mesh) model (2) of the targeted tissue is converted to a smooth parametric surface (5). The computer model is then sliced for the layer-based 3D bioprinting process. To support the live longitudinal multicellular aggregates (11) to be bioprinted, a novel self-supporting methodology is developed. Said self-supporting methodology is used to calculate corresponding locations for both longitudinal multicellular aggregates (11) and the support structures (12). The bioprinting topology is generated in order to 3D bioprint the targeted tissue model directly from medical images, thus longitudinal multicellular aggregate (11) paths and support structure (12) paths are generated. Said longitudinal multicellular aggregate (11) and support structure (12) paths are used to control the bioprinter for 3D printing of a biomimetic network construct. The details of the proposed methodology are given below.

Figure 1:
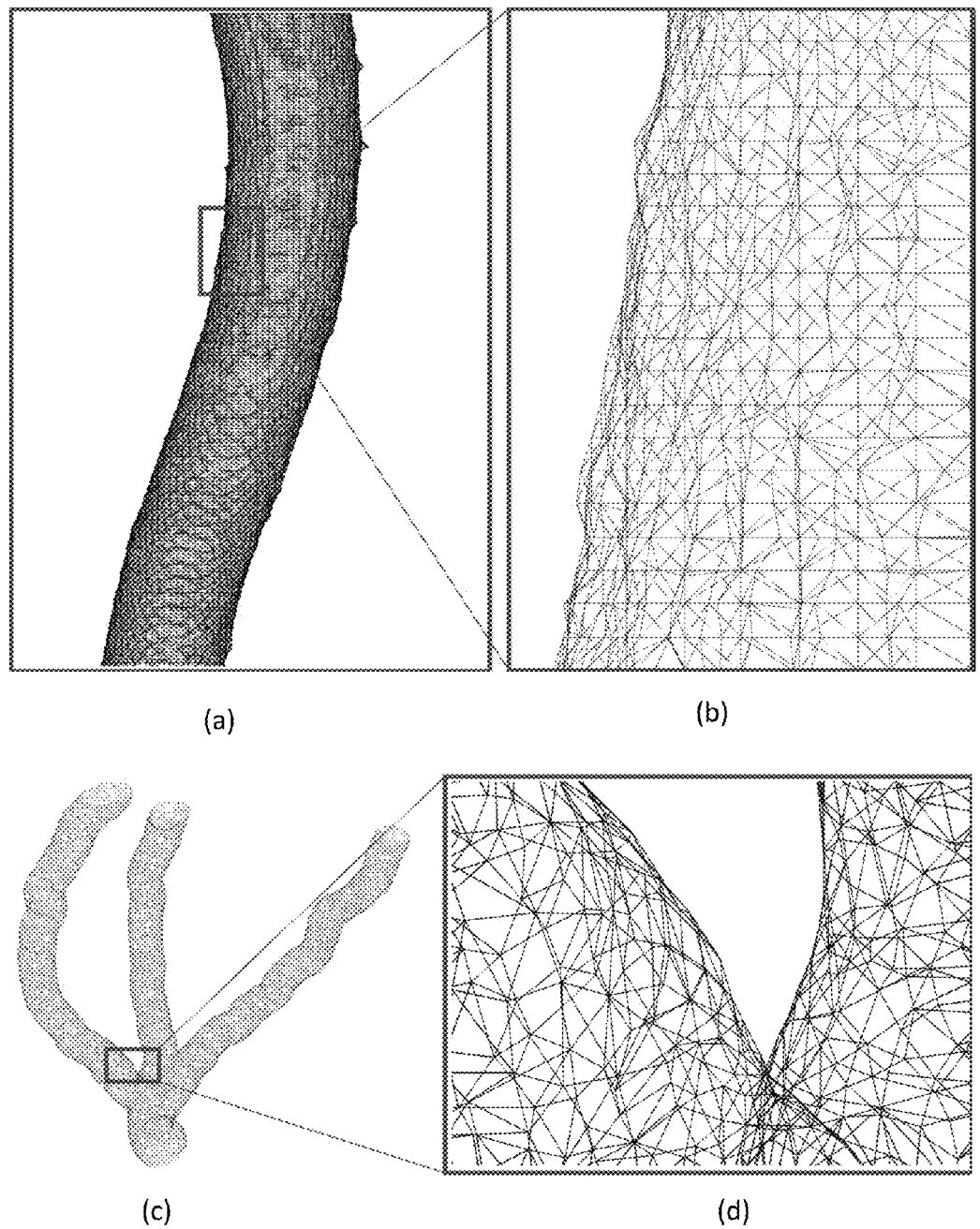
FIG. 1 represents an STL models (a, c) of two sample targeted tissues, and respective detailed views (b, d) of said STL models for use in the method according to the present invention.

To be able to 3D bioprint an anatomically correct biomimetic network, a medical image of the original geometry of the targeted tissue must be captured and transformed into a computer aided model (CAD) of the tissue. Three-dimensional medical images such as Magnetic Resonance Imaging (MRI) and Computer Tomography (CT) can be used for capturing the anatomically correct forms of internal organs and tissues. As an example of a suitable application according to the present invention, the main abdominal aorta model from a sample MRI data is used to highlight the proposed methods' capabilities for 3D bioprinting of macrovascular structures. In order to obtain 3D computer models of a targeted tissue, MRI or CT images are segmented using suitable software, e.g. the Mimics software. To demonstrate the proposed methodology, a part of tissue (e.g. abdominal aorta) model is obtained from a set of MRI slices. A suitable imaging software was used for segmentation of the tissue. The segmented region of the tissue is then converted into a 3D model. Initial geometric information of the tissue structure is then represented as a computational model (2), preferably a mesh model or a stereolithography (STL) model. The STL models are generated by tessellating the outer surface of the mesh model (2) with triangles. STL models of targeted tissues (here, sections of human blood vessels), which is suitable to be used for computer-aided biomodeling methodology described below, is shown in FIG. 1 (a) for a non-branched target tissue and (c) for a branched target tissue. Detailed views taken from said models are shown in FIG. 1 (b) for said non-branched and (c) branched target tissues.

Figure 3:
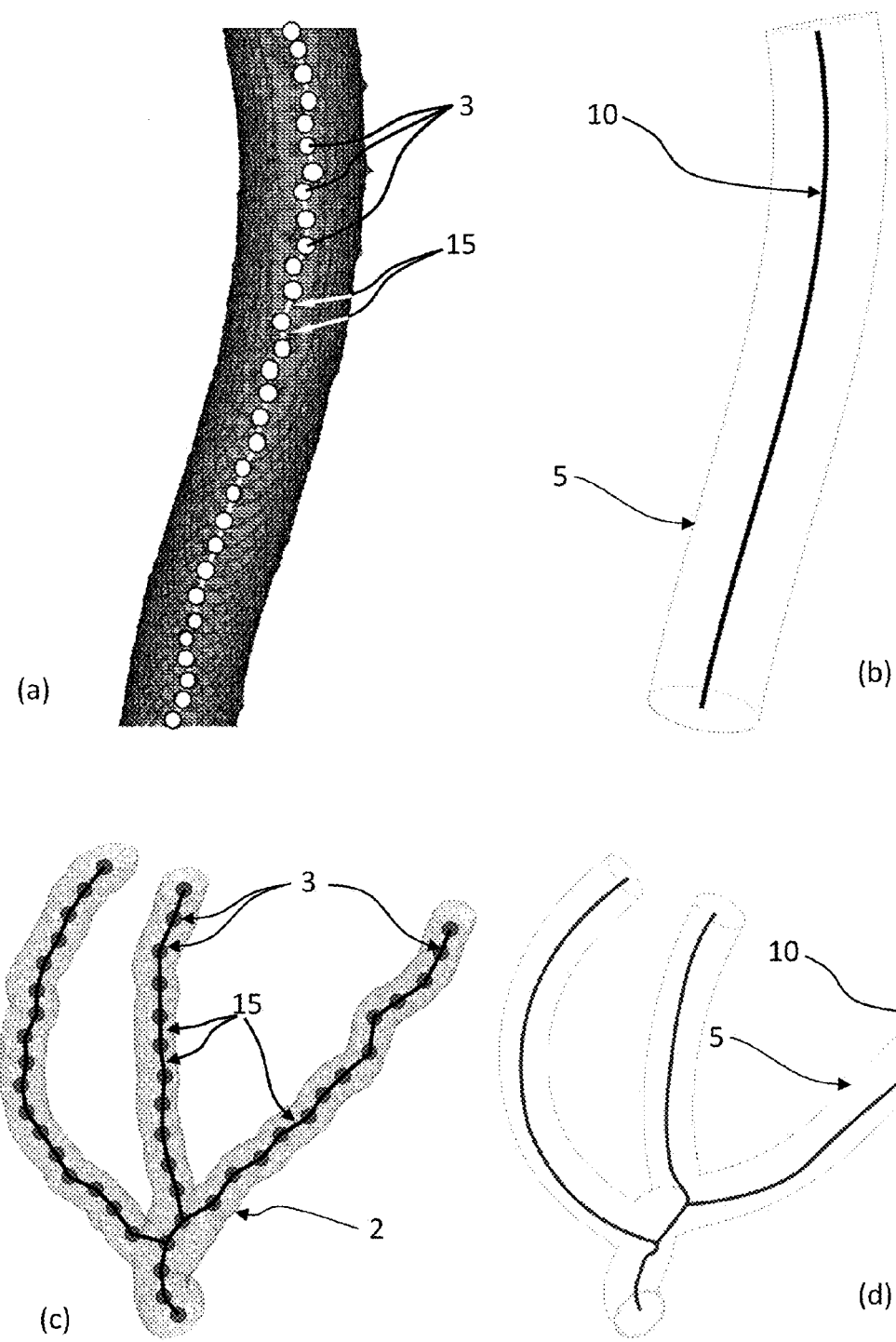
FIG. 3 shows representative drawings (a, c), and respective detailed views from said drawings (b, d) for further understanding the method according to the present invention.

Captured STL models of targeted tissues are not smooth and they could contain numerous polynomial (here, triangular) facets (8). For tool path planning as well as for optimization for 3D bioprinting, the resultant STL model of the targeted tissue requires to be represented by parametric surfaces. A novel biomodeling method is developed to convert these mesh structures having triangular facets into smooth parametric surfaces suitable for 3D bioprinting. The parametric representation of the targeted tissue model also eliminates any noise stemmed from the previous segmentation phase. A representative drawing for understanding said biomodeling method of marching through section curves resulting of a centerline curve (10) of converting STL model to smooth parametric surfaces is shown in FIG. 3, and another representative drawing for further understanding said biomodeling method is shown in FIG. 3. To that end, section curves (1) are generated from the mesh model (2). Center points (3) of each section curve (1) (contour) are then calculated. Generated center points (3) are used for approximation of a centerline curve (10). Then, smooth parametric surfaces (5) are generated along a trajectory of calculated centerline curve(s) (10).

Figure 2:
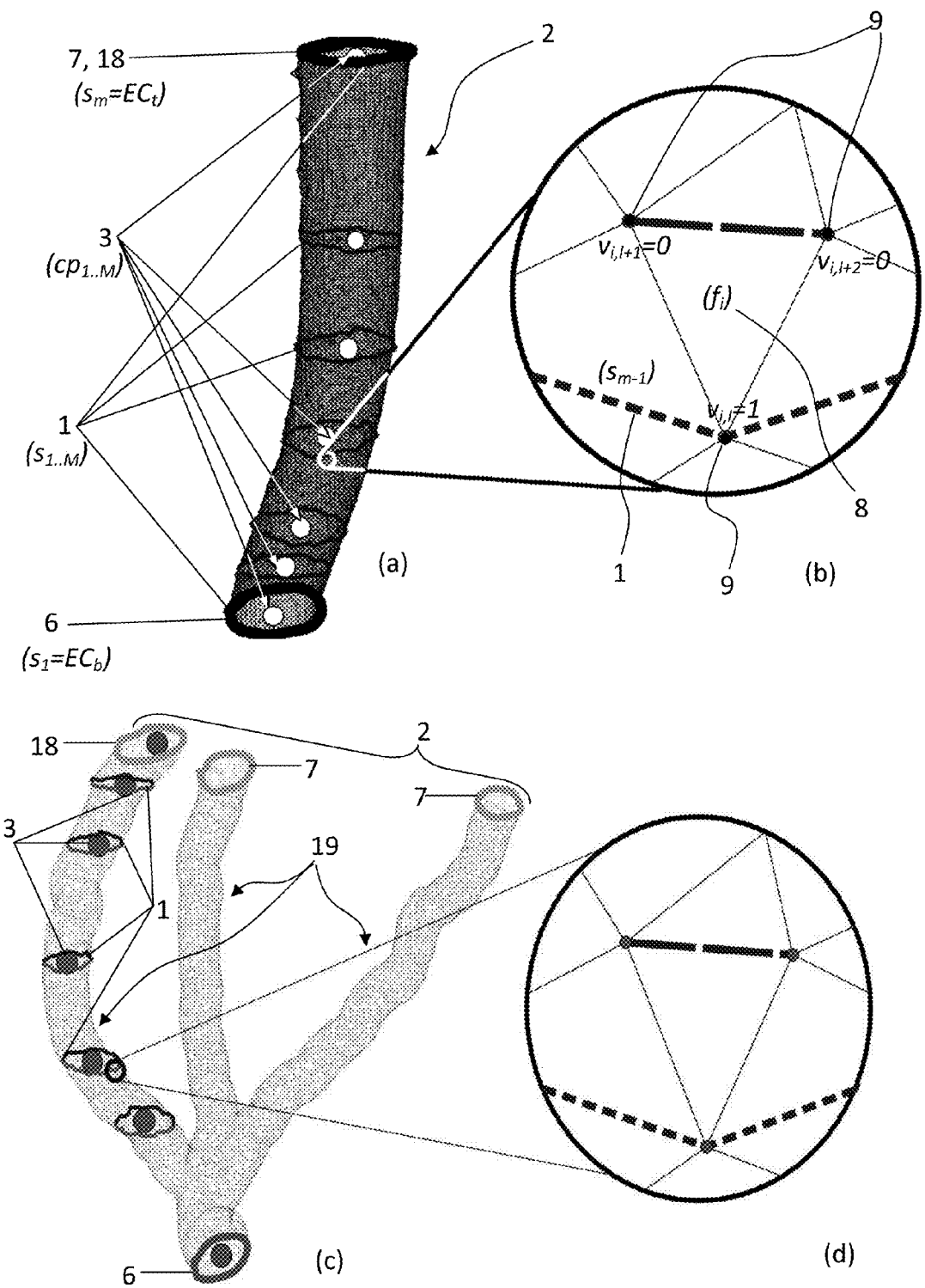
FIG. 2 shows representative drawings for understanding the biomodeling method of marching through section curves resulting of centerline curves of converting STL models to smooth parametric surfaces according to the present invention.

To identify boundaries of said model (2) of the targeted tissue as an input, edge curves, i.e. bottom curve (6) $(EC_b)_{b=1}$ and top curve(s) (7) $(EC_t)_{t=1\ldots T}$ are defined as end section curves, as shown in FIG. 2. Said curves are basically the starting and ending branched section curves of the STL model of a targeted tissue. To initiate the algorithm and the centerline curve (10) extraction process, the bottom section curve (6) $(EC_b)$ is used as the input. As STL model is represented with polynomial (here, triangulated) surfaces, all facets (8) $\{f_i\}_{i=1\ldots I}$ have multiple (here, three) vertices (9) and each vertex (9) can be a part of several other facets (8) as shown in FIG. 2 (b). Initially, all the vertices (8) $V=\{v_{i,l}\}_{l=1\ldots L}$ are unvisited when the algorithm starts to progress, unvisited vertices get marked as 'visited' when they get visited i.e. when they contribute to form a section curve (1) with respect to an intended marching direction of algorithmic calculations. The visiting operation is important in order to visit each vertex (9) only once, and to continue marching on an intended marching direction. A set of section curves (1) is represented as $S=\{s_m\}_{m=1\ldots M}$, and each section curve (1) is defined with N vertices (9) (points) represented as $S_{m,n}=\{s_{m,n}\}_{n=1\ldots N}$. Since the end points of facet edges from the bottom section curve (6) $(EC_b)$ belong to a set of elements of a list of vertices (9), the algorithm marks said vertices as 'visited' in order to proceed without re-visiting any vertex (9). Connecting all N vertices (9) respectively results in a section curve (1) which is a closed polyline curve, thus we refer the sections as section curves. Furthermore, for each section curve (1) it is defined a center point (3) $CP=\{cp_m\}_{m=1\ldots M}$ reflecting the area weight-based center points (3) for each corresponding section curve (1), and respective radius values $R=\{r_m\}_{m=1\ldots M}$ reflecting the radius of a maximally-inscribed sphere of each section curve (1). An algorithm is developed to compute the area weight-based center points (3) and respective radius values according to those vertices of the section curves (1).

After several vertices (9) are marked as 'visited', the algorithm starts to march through the section curves starting from the bottom section curve (6) $(EC_b)$ until it reaches to the top section curve(s) (7) $(EC_t)$. If there are multiple closed section curves at a said section, the developed algorithm marks the previous section curve as starting point of said branched section curves. After one of the top section curves (7) is reached, the iteration continues from the starting point until reaching to all the top section curves (7). As marching from one section curve to another, if only one vertex (9) of a facet (8) is marked as 'visited', than that means remaining vertices (9) (here, the other two vertices of a triangular facet), as well as the edge connecting them, have to be a component of a next polyline i.e. a next section curve (1). Therefore, connecting said edges i.e. vertices (9) in topological order will give a closed loop, thus a section curve (1).

FIG. 2 (b) shows the marching process with a visited vertex $v_{i,l+1}$ and a part of a calculated section $s_{m-1}$ (small dashed curve), therefore unvisited vertices and $v_{i,l+2}$ are to be on a subsequent section $s_m$ (big dashed curve). FIG. 2 (a) shows several section curves (1) and several center points (3) of section curves (1) for the tissue model. Furthermore, a section curves' maximally-inscribed sphere's radius will be the radius value for a corresponding center point (3).

The computation of Cartesian coordinate of a center point (3) and respective radius value for the $m^{th}$ section curve (1) with N vertices (9) is preferably as follows:

$S_{m,n}=\{s_{m,n}\}_{n=1\ldots N}$ A set of N points in the $m^{th}$ section $$cp_m = \left(\frac{\sum_{n=1\ldots N} s_{m,n}(x)}{N}, \frac{\sum_{n=1\ldots N} s_{m,n}(y)}{N}, \frac{\sum_{n=1\ldots N} s_{m,n}(z)}{N}\right) \quad \text{(Equation 1)}$$

$$r_m = \min_{n=1\ldots N}(\|\overline{s_{m,n}, cp_m}\|)$$

When each top section curve (7) is reached by marching through the section curves (1), the algorithm approximates a B-spline centerline curve (10) preferably using Cartesian coordinates of the center points (3). Then, the algorithm builds a B-spline curve, which will be the centerline curve (10) for the parametric surface (5). Mathematically, this parametric B-spline centerline curve (10) is preferably defined as:

$$CC(u) = \sum_{i=1}^{m} N_{i,p}(u) \cdot cp_i$$

$$0 \leq u \leq 1$$

Where B-spline basis function is:

$$N_{i,0}(u) = \begin{cases} 1 & \text{if } u_i \leq u < u_{i+1} \\ 0 & \text{otherwise} \end{cases} \quad \text{(Equation 2)}$$

$$N_{i,p}(u) = \frac{u - u_i}{u_{i+p} - u_i} N_{i,p-1}(u) + \frac{u_{i+p+1} - u}{u_{i+p+1} - u_{i+1}} N_{i+1,p-1}(u)$$

Where $cp_i$'s are the central points (3), and the $N_{i,p}(u)$ are the $p^{th}$-degree B-spline basis functions as defined above with a knot vector $U=\{u_0,\ldots,u_m\}$ where $u_i$'s be a non-decreasing sequence of real numbers.

The B-spline parametric surface (5) $S_k(u,v)$ of a tissue model is generated using said centerline curve(s) (10) for each branch (19) with respect to the average radius value of relevant center points (3) as shown in FIG. 3. This operation basically sweeps a planar closed curve along a trajectory curve, as the centerline curve (10). Denote the trajectory centerline curve by $CC_b(u)$ and the planar closed curve by $T(v)$. A general form of the swept surface is given by:

$$S_k(u,v)=CC_b(u)+M(u)T(v)$$

Where $0 \leq u \leq 1$ and $0 \leq v \leq 1$ $$T(v)=(r_{avg}\cos(v), r_{avg}\sin(v)) \quad \text{(Equation 3)}$$

Where $M(u)$ is a 3×3 matrix incorporating rotation and non-uniform scaling of $T(v)$ as a function of u.

A smooth tissue model (e.g. a blood vessel model) from the mesh model is determined using below algorithm.

Algorithm 1: Generating NURBS (non-uniform
rational B-spline) Surface(s)

Input:
$M_k$:                              Mesh
$EC=\{EC_{b,t}\}_{b=1,\ t=1..T}$:   a set of a bottom and top
                                    edge curves of a Mesh
$F=\{f_i\}_{i=1..I}$:               a set of faces on the Mesh
$V=\{v_{i,l}\}_{l=1..L}$:           a set of vertices on the Mesh
Output:
$S_k(u,v)$:                         generated B-spline surface(s)
Start
Initialize i ← 1, m ← 1
$S_1$ ← $EC_b$
Mark vertices of $S_1$ as 'visited' in set V
$cp_m$ ← calculate $cp_m$ using Equation (1)
$r_m$ ← calculate $r_m$ using 'Equation 2'
m ← m+1
From $EC_b$ To all $EC_{t=1..T}$ { //for all branches
  For (m=2 to M) {//for all section curves
    For (i=1 to I) {//for all faces
      If $(v_{i,l} + v_{i,l+1} + V_{i,l+2} = 1$ // only one vertex of a face $f_i$ is visited)
        Then determine subsequent section's ($S_m$) points (vertices)
If $v_{i,l}$ =0 Then $S_{m,n}$ ← $v_{i,l}$
If $v_{i,l+1}$ =0 Then $S_{m,n+1}$ ← $v_{i,l+1}$
If $v_{i,l+2}$ =0 Then $S_{m,n+2}$ ← $v_{i,l+2}$
    }
  }
Mark vertices of the $S_m$ curve as 'visited' in set V
$cp_m$ ← calculate $cp_m$ using Equation (1)
$r_m$ ← calculate $r_m$ using 'Equation 2'
}
$CC_b(u)$ ← approximate a centerline curve with the control points using 'Equation 2'
$S_k(u,v)$ ← Build the surface along $CC_b(u)$ with respect to its control point's average radius value using Equation (3)
}
End Algorithm 1 is very critical in biomimetical modeling of a targeted tissue model for 3D bioprinting topology calculation for both longitudinal multicellular aggregates (11) and support structures (12).

In this method, complex geometries of cellular networks are bioprinted with self-supporting hydrogels. Not only because of its complex geometry, but also due to dynamic structures of both cells and hydrogels, it is challenging to build such structures in 3D. In order to fabricate anatomically correct networks using longitudinal multicellular aggregates (11), which are mechanically-weak, should be supported by support structures (12) to allow cell fusion. In this section, algorithms are developed to determine an optimum 3D bioprinting topology to control the bioprinter directly without any human intervention.

Figure 4:
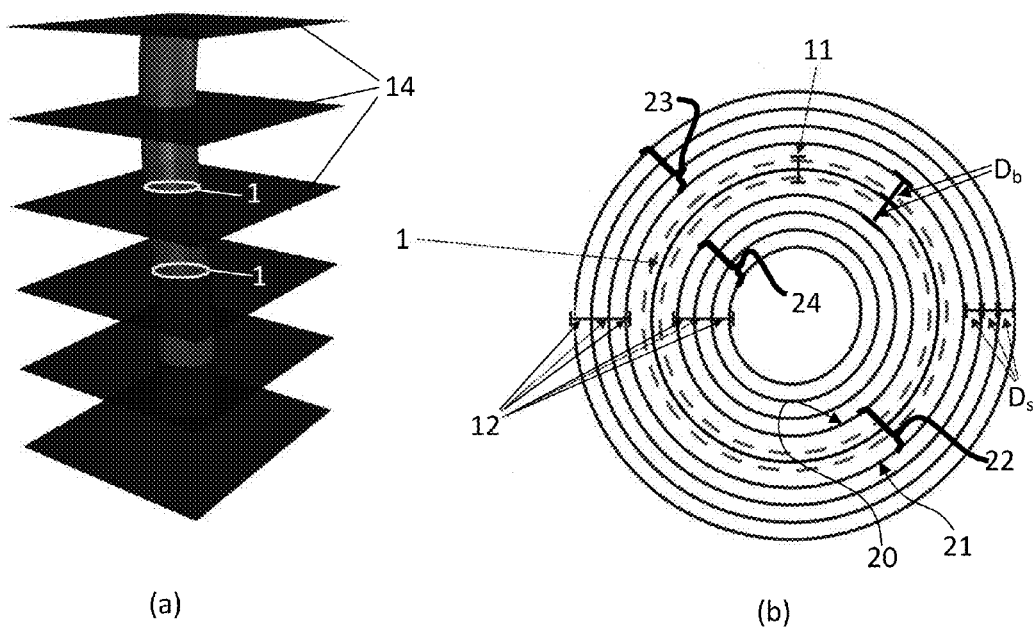
FIG. 4 represents (a) several layers on a smooth surface model and (b) plan view of a bioprinted layer according to the present invention.

FIG. 4 (a) shows several layers on said smooth surface (5) model where two of section curves (1) on said smooth surface (5) model are emphasized. Longitudinal multicellular aggregate (11) is to be used layer-by-layer for obtaining targeted network (100) in accordance with said model (2). After a smooth surface (5) model of a targeted biological tissue (here, unbranched and branched blood vessels) $S_k$(u, v) is generated as explained above, an optimum 3D bioprinting topology is to be determined. Path planning for both longitudinal multicellular aggregate (11) and support structures (12) is calculated.

Also lengths of longitudinal multicellular aggregates (11) and support structures (12) to be used for constitution of each bioprinted layer (22) are calculated, such that said closed loops of longitudinal multicellular aggregates (11) and support structures (12) are without interruption.

The support structures (12) used in exemplary experiment according to the present invention was prepared according to the following sequence:

A pre-determined amount of above-explained biocompatible, bio-inert, thermo-reversible hydrogel material kept under temperature preferably within the range of 50-80° C., more preferably within the range of 65-75 ° C. where it is in a liquid form, is aspirated into a capillary such that said amount fills a predetermined length of said capillary, which length is equal to a predetermined length of a support structure (12), said capillary is cooled to about 4° C. for gelation of said material mixture, preferably by contacting outer surface of said capillary with cold liquid e.g. phosphate buffered saline, said material gelates in said capillary, thus a support structure (12) in a pre-determined shape and length is formed.

Preferably, said aspiration is performed using an automated bioprinter, wherein said predetermined length of said capillary is equal to a respective length for a non-interrupted closed loop support structure (12) in a certain layer (22) to be bioprinted.

Figure 5:
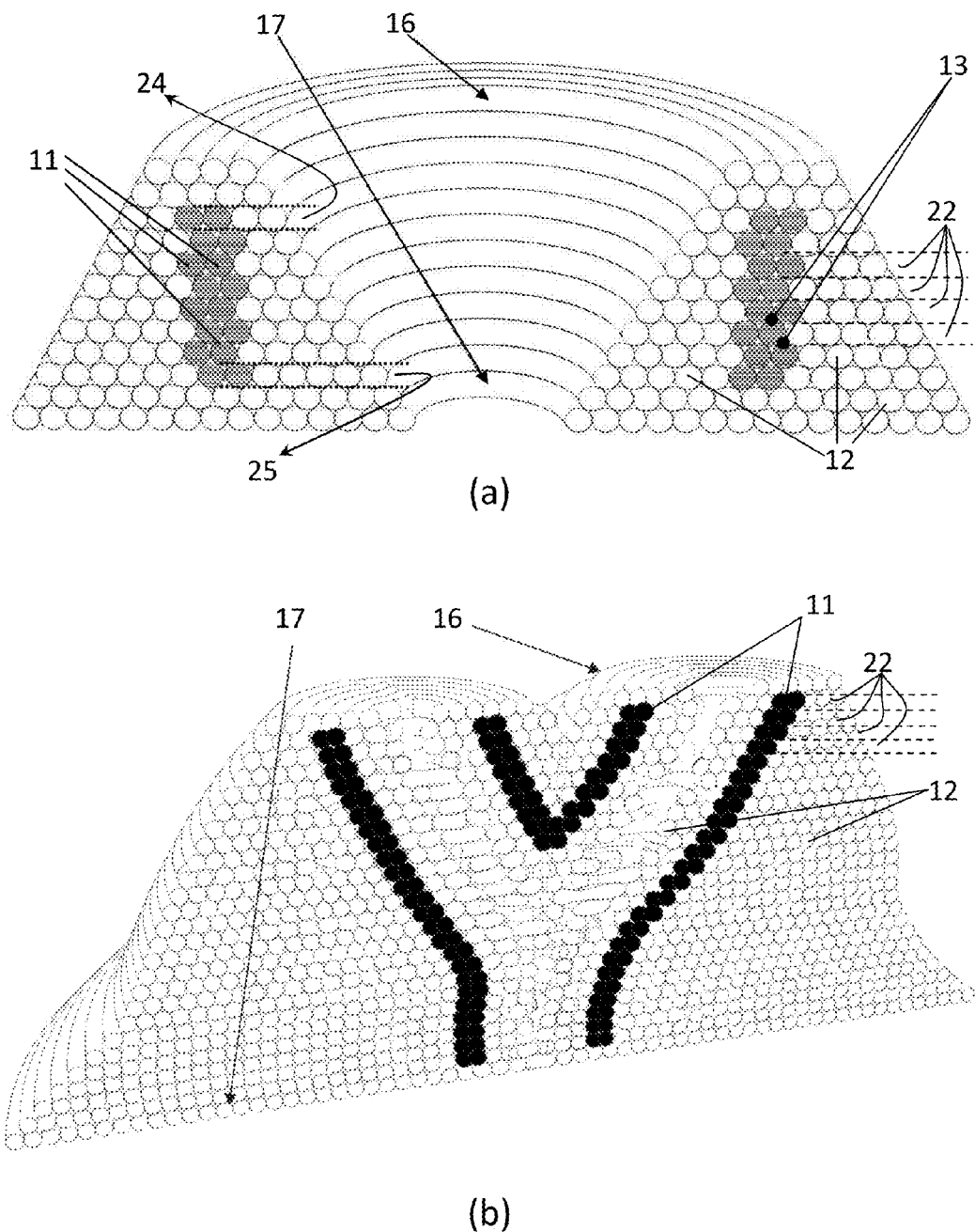
FIG. 5 represents a cross-section of modeled artificial biological tissue networks according to the present invention.

Both longitudinal multicellular aggregate (11) and support structures (12) are printed by a capillary (or respective capillaries), which capillary is preferably made of glass or another suitable bio-inert solid material, in a gel-like form layer by layer to form the 3D tissue network. Since longitudinal multicellular aggregates (11) are not self-shape preserving, both longitudinal multicellular aggregates (11) and support structures (12) should accordingly be placed on 'valleys' (13) of preceding layers as shown in FIG. 5 in order to provide cell fusion and to print anatomically-correct model of the original tissue.

Because the network (100) is to be printed layer by layer, height increments between consecutive bioprinted layers (22) should be approximate to the diameter of the capillary tubes (shown in FIG. 1). The total number of layers (totalLayers) is calculated by dividing total surface height to the capillary diameter. The surface representation of the tissue is then sliced with successive calculative layers (14) which resulted in contour curves $C_{j,0}(t)=\{c_{j,0}\}_{j=1\ ...\ totalLayers}$ for each calculative layer (14) as shown in FIG. 4 (a); said calculative layers (14) are theoretical horizontal planes which are to be parallel to a uniformly flat surface for constructing the network (100) thereon. The number of support structures for each layer (14) is then determined by the $maxStep_j$ values obtained from:

$maxStep_{j=totalLayers}$=topSupport where topSupport is the number of support structures (12) on top layer which is input by the user; totalLayers is the number of layers including bottom layer (25) and top layer (24); and j is the layer number which is the independent variable here, where j=totalLayers for the top layer (24) and j=1 for the bottom layer (25). Since $maxStep_j$ values are non-decreasing from the top layer (24) through the bottom layer (25), which provides safe elevation between successive bioprinted layers (22).

The general shape of the targeted tissue on each bioprinted layer (22) is conserved and deformation of weak longitudinal multicellular aggregates (11) under gravity or any outer disturbance is prevented by offsetting each contour curve using maxStep, value of each specific layer on the horizontal plane. Offset amounts of contour curve(s) $O_{j,J}=\{o_{j,i}\}_{i=1\ ...\ maxStep\ j}$ for a layer can be found by the following formula:

$$o_{j,J}=((maxStep_j/2)-(i-1)) \times d_{capillary} \qquad \text{(Equation 4)}$$

Where $d_{capillary}$ is capillary the diameter of the capillary used.

The initial offset amount for a layer is strictly positive, resulting in exterior offset curves. However, offset amount is dropped by the capillary diameter for each successive support structures on that layer. Therefore, upon reaching (maxStep$_j$/2) support structures, offset amount will become negative resulting in interior offset curves. Thus, cellular aggregates are supported by support structures from both inside (20) and outside (21) of the network (100). As $c_{j,0}(t)$ defines a contour curve of the surface on a given height and a curve parameter t, then the offset curves with respect to the $o_{j,i}$ will be:

$$c_{j,i}(t) = c_{j,0}(t) + o_{j,i} \vec{N}_{j,i}(t)_{i=1 \ldots maxStep_j} \quad \text{(Equation 5)}$$

Where $N_{j,i}(t)$ is unit normal vector on curve $c_{j,0}(t)$ at a parameter t

If multiple support structures $c_{j,i}(t)$ intersect at a same layer, they are joined and trimmed to form one closed loop of support structure at respective layer.

A number (here, two) of pieces on a bioprinted layer (22) of a respective calculative layer (14), which are represented as the dashed ones in FIG. 4 (b), with respect the maxStep$_j$ value, are placed as longitudinal multicellular aggregates (11) and the remaining pieces as support structures (12) in order to effectively mimic the original dimensions of a target tissue and to provide better coverage of cells. Said number of longitudinal multicellular aggregates (11) for a calculative layer (14) i.e. on a bioprinted layer (22) is calculated by dividing the wall thickness of targeted tissue to the diameter of the longitudinal multicellular aggregate (11), and rounding the result up to nearest integer.

For each bioprinted layer (22), support structures (12) are printed first, and then longitudinal multicellular aggregate (11) is printed in order to prevent cell outflow and to preserve anatomically correct shape of the modeled tissue. As the $o_{j,i}$'s for the $j^{th}$ layer keeps decreasing by $d_{capillary}$ amount at each increment on i, support structures on a layer are printed from the outermost one, to the innermost one.

After determining layouts for longitudinal multicellular aggregate (11) and support structures (12) for each bioprinted layer (22), the 3D bioprinting path (topology) for cell-biomaterial is calculated. Commands to control the bioprinter for constructing the network (100) are saved to a file as described in Algorithm 2 below. Then, longitudinal multicellular aggregate (11) pieces and support structures (12) will be 3D printed layer by layer. Diameters of longitudinal multicellular aggregate (11) and support structures (12) are represented in FIG. 4 (b) with $D_b$ and $D_s$, respectively.

Thus, a network (100) is composed of longitudinal multicellular aggregates (11) and support structures (12) that keep said longitudinal multicellular aggregates in the designed shape as intended. According to the present invention, each bioprinted layer (22) is sufficiently supported for stable cell aggregate printing as required, since the longitudinal multicellular aggregate (11) has less strength in comparison with an original biomaterial of the targeted tissue.

---

Algorithm 2. Self-supporting model
generation of support structures

---

Input:
S$_k$(u,v): generated NURBS Surface
d$_{capillary}$: diameter of used capillary
topSupport: number of support structures on top layer (user input)

---

Algorithm 2. Self-supporting model
generation of support structures

---

Output:
Finalized vascular model, with support structures
Path planning for 3D-Bioprinting (a compatible script file for the 3D-Bioprinter)
Start
Initialize totalLayers ← (surfaceHeight/d$_{capillary}$) + 1, j ← 1,
n ← 1, i ← 1, contourlevel ← 0
Initialize maxStep$_j$ ← topSupport + totalLayers − j
For (j=1 to totalLayers) {
   contourLevel ← contourLevel + d$_{capillary}$
   If (c$_{j,0}$ ← contouring the surface from a given contourLevel, results in closed curve(s)) Then {
     For each c$_{j,0}$/or c$_{b,j,0}$ {
       Initialize o$_{j,i}$ ← (maxStep$_j$/2) x d$_{capillary}$
       For (i=1 to maxStep$_i$) {
c$_{j,i}$ ← offset c$_{j,0}$ by o$_{j,i}$ using Equation (5)
       Initialize curveLength ← length of (c$_{j,i}$)
If (curvelength < minSegmentLength) Then {Exit For}
// for prevention of self-intersection in offset operations
       If (i = maxStep$_j$/2 or i = (maxStep$_j$/2)+1) Then {
       Store c$_{j,i}$ and curveLength in the bioprinter control file as a cellular structure}
       Else {Store c$_{j,i}$ and curveLength in the bioprinter control file as a support structure}
o$_{j,i}$ ← calculate o$_{j,i}$ using Equation (4)
       }
maxStep$_j$ ← topSupport + totalLayers − j }
   }
}
End

---

Here, the term 'minSegmentLength' represents the length of a straight longitudinal piece (longitudinal multicellular aggregate or support structure) suitable to be bent or arched to form a closed loop without damaging said piece, and further suitable to form a pre-determined geometry for a certain function. If said piece is a longitudinal multicellular aggregate (11), said function can be maintaining a sufficient inner diameter allowing support structure to be placed; or if said piece is a support structure (12), said function can be approximately matching geometrical center points of both bases of longitudinal piece of support structure to form a proper closed loop for properly supporting an adjacent longitudinal multicellular aggregate loop (representing a section curve) of the same calculative layer (14). Said 'suitability to be bent or arched without damaging a piece' depends on robustness (e.g. resilience) and shapes (i.e. geometries) of longitudinal pieces (11, 12) of longitudinal multicellular aggregate and support structure including their lengths and approximate diameters (or diameters for cylindrical pieces).

The implementations of both algorithms and methodologies for a tissue which are to be used for 3D hybrid bioprinting with above-mentioned mixture of cells and hydrogels will be presented below.

A suitable programming language e.g. Rhinoscript can be used for generating the above algorithms. Initial geometries of targeted tissues are obtained by using suitable software e.g. Mimics and the patient's MRI data. In order to represent an STL model by freeform surface information, Algorithm 1 was used which extracts skeleton curves based on center lines (15) of the mesh model (2) and said algorithm generates smooth parametric surfaces (8) from said model (2). Then, in Algorithm 2, path planning for both longitudinal multicellular aggregate (11) and support structures (12) is calculated. Final outputs of the developed algorithms are 3D bioprinter instructions controlling the longitudinal multicellular aggregate (11) and support structure (12) heads to build the network (100) constructs layer by layer directly from the generated computer model.

The whole tissue network surface model, which is extracted from an STL file obtained by Algorithm 1, was 50 mm high and its diameter is around 9 mm for the above explained experiment. In this step, dimensions of the network were exactly mimicked in bioprinting of both longitudinal multicellular aggregate (11) pieces and support structures (12). A partial tissue model (for the examples presented in the figures, unbranched and branched human blood vessels) is extracted and its path planning for 3D bioprinting is obtained by Algorithm 2. With the above explained experiment, the developed methods according to the present invention are used for bio-printing of a network (100) comprising longitudinal multicellular aggregates (11) of a certain diameter (450 μm). Longitudinal multicellular aggregates (11) and support structures (12) are 3D printed layer-by-layer according to the developed Self-Supporting method. The longitudinal multicellular aggregates (11) are successfully printed at the valleys (13) formed by the support structure (11). The 3D printed longitudinal multicellular aggregates (11) were perfectly supported by hydrogel.

To 3D bioprint continuously and to minimize the stress imposed on the cells of the longitudinal multicellular aggregate (11), we omitted the capillary incubation and manipulation steps. In accordance with the present invention, we switched to a bottom-up continuous bioprinting protocol design, which is explained above in detail. This new approach also allowed us to obtain artificial biological tissue networks (100) with enhanced longitudes, made printing possible in multiple bioprinted layers (22), and in any complicated forms of target tissues. Using bottom-up continuous bioprinting, we were able to design and 3D print longitudinal multicellular aggregates (11) corresponding to any size and shape of a targeted tissue.

In other words; for implementation of the present invention, novel computer aided algorithms are developed in order to 3D bioprint cell and support structures for scaffold-free tissue engineering e.g. macro-vascular tissue engineering. The tool path design and 3D printing parameters are optimized for an anatomically correct 3D printing. After segmentation of a part of a targeted tissue using medical images and segmentation software, the captured geometry of said targeted tissue was converted to a computer-aided design model, i.e. model. In order to develop optimum path planning, parametric surfaces are generated from said model. For 3D bioprinting of longitudinal multicellular aggregates directly from medical images of a targeted tissue model, a novel self-supporting methodology was developed with computational algorithms. Support structures and longitudinal multicellular aggregates are successfully printed with the developed self-supporting methodology. The developed algorithms are implemented in a CAD software package, Rhino3D using Rhinoscript language. The generated commands from the developed algorithms were used to control the bioprinter. To increase the cell viability, a small amount of appropriate medium is preferably dropped on printed longitudinal multicellular aggregate pieces during printing process.

Preferably, the surface on which the network (100) is bioprinted is covered with a continuous support layer (17) which prevents longitudinal multicellular aggregate (11) from contacting said surface. Additionally, a covering support layer (16) is placed on bioprinted network (100). Preferably, said continuous support layer (17) and covering support layer (16) and support structures (12) comprise said appropriate medium to provide increased cell viability.

In a further embodiment of the method according to the present invention, an automated dropping step of said appropriate medium is added to said method.

Modeled parts of human blood vessel constructs were successfully 3D bioprinted in accordance with the methods of the present invention.

Thus, a self-supporting scaffold-free artificial hollow biological tissue network for replacement of living tissue is provided. Furthermore, an artificial biological tissue network is obtained with a high reproducibility and without requiring any manual intervention. Said network is constructed in bottom-up direction. Additionally, said network achieves a natural mechanical strength in a shorter time with respect to the prior art. A method for obtaining such artificial biological tissue network is provided.

We claim:

1. A self-supporting network for replacement of a living tissue, said network is an artificial hollow biological tissue network comprising a plurality of elongate longitudinal multicellular aggregates arranged in a plurality of bioprinted layers which are located on top of one another, further comprising an inner surface and an outer surface, wherein
   at least one of said bioprinted layers is in shape of a planar closed loop such that a conduit for conveying fluids is defined by such bioprinted layer, and
   said longitudinal multicellular aggregate is a mixture of at least two cell types;
   further wherein said network is a branched conduit comprising at least two branches converged on at least one sector of said network; provided that the network comprises a branch which is out of plane with respect to the other branches of the network when the network is laid on a planar surface.

2. A network according to the claim 1, wherein each closed loop of said longitudinal multicellular aggregate is in contact with biocompatible support structures from both said inner surface and said outer surface for serving as a mold during a maturation process of the biological tissue network.

3. A network according to the claim 1, wherein said longitudinal multicellular aggregate comprises at least one type of cells selected from a group of cell types consisting of fibroblasts, eldothelial and smooth muscle cells.

4. A network according to the claim 3, wherein said longitudinal multicellular aggregate further comprises stem cells.

5. A network according to the claim 1, wherein each longitudinal multicellular aggregate is in direct cell-to-cell contact with at least one adjacent longitudinal multicellular aggregate.

6. A network according to the claim 1, wherein said longitudinal multicellular aggregates are completely or partially cohered with each other.

7. A network according to the claim 1, wherein said longitudinal multicellular aggregate has a length/diameter aspect ratio in the range of 20 to 250.

8. A network according to the claim 7, wherein said longitudinal multicellular aggregate (11) has a diameter within the range of 100 to 2500 micrometers.

* * * * *